(12) United States Patent
Lube et al.

(10) Patent No.: US 6,656,484 B1
(45) Date of Patent: Dec. 2, 2003

(54) KIT ASSEMBLY AND METHOD FOR PERFORMING A COSMETIC NAIL TREATMENT

(76) Inventors: Rose Mary Lube, 7431 NW. 1St., Margate, FL (US) 33063; Thomas Cesare Rao, 7431 NW. 1St., Margate, FL (US) 33063

( * ) Notice: Subject to any disclaimer, the term of this patent is extended or adjusted under 35 U.S.C. 154(b) by 0 days.

(21) Appl. No.: 09/777,188

(22) Filed: Feb. 5, 2001

(51) Int. Cl.$^7$ .............................. A61K 7/00; A61K 7/04; A45D 29/00
(52) U.S. Cl. .............................. 424/401; 424/61; 132/73
(58) Field of Search ...................... 424/401, 61; 132/73

(56) References Cited

U.S. PATENT DOCUMENTS

| | | |
|---|---|---|
| 2,162,155 A | 6/1939 | Calvin |
| 2,239,040 A | 4/1941 | Holmes |
| 3,898,357 A | 8/1975 | Miller et al. |
| 4,194,617 A | 3/1980 | Bandell |
| D339,657 S | 9/1993 | Walker-Shell |
| 5,645,090 A | 7/1997 | Juhl et al. |
| 5,782,248 A * | 7/1998 | Chang ........................ 132/200 |

* cited by examiner

Primary Examiner—Shelley A. Dodson
(74) Attorney, Agent, or Firm—Malloy & Malloy, P.A.

(57) ABSTRACT

A kit assembly and method of performing a cosmetic treatment on a person's nail preferably, but not exclusively, in the style of a the french manicure and/or pedicure. The kit assembly includes a plurality of compositions, preferably in solution form, at least two of which are polishes of different colors and wherein one of the plurality of compositions includes a shaping solution applied to a predetermined portion of the nail in a precise but easily accomplished manner so as to create a demarcation segment between a tip of the nail and a base of the nail. A shaping implement used to apply the shaping solution may include a brush having a brush head comprising a plurality of bristles collectively dimensioned and configured facilitate the precise forming of the demarcation segment into a "perfect curve" or curvilinear configuration which substantially corresponds to the natural transverse contour of the nail. The demarcation segment or curved line thereby provides a visual boundary between the tip and the base of the nail which are visually distinguishable due, at least in part, the application of the different color polishes. The plurality of the solutions of the kit assembly may also include a top coating formulated to protect and add a lustrous sheer to the treated mail.

16 Claims, 2 Drawing Sheets

KIT ASSEMBLY AND METHOD FOR PERFORMING A COSMETIC NAIL TREATMENT

BACKGROUND OF THE INVENTION

1. Field of the Invention

This invention relates to a kit assembly and method of performing a cosmetic treatment on the nails of a person preferably, but not exclusively, in the style of a french manicure or pedicure, through the utilization of a shaping implement structured to apply a shaping solution to predetermined portions of the nail. A demarcation segment in the form of a "perfect curve" is thereby created, which visually segregates the tip and base portions of the nail and which characterizes the style of the french manicure or pedicure.

2. Description of the Related Art

The cosmetic treatment of women's nails, performed in order to enhance their aesthetic appearance, has been known and practiced in various societies throughout the world for hundreds of years. Typically, known cosmetic nail treatments generally include the application of one or more color polishes to the nail. Decorative additions included in known cosmetic treatments include additional "art work" such as painting small objects on the nails or, even more recently, applying decorative decals to the nail in order to further enhance their appearance. The cosmetic treatment of nails typically includes a wide variety of different styles or designs, depending upon the current, preferred appearance of a women's nails. However, one cosmetic style which has endured for over fifty years is known as the "french" manicure or pedicure style. This style may be generally characterized as applying a substantially white or off-white polish in a uniform manner to the tip of the nail only and applying a polish of visually distinguishable color which may be translucent, to the remainder or base portion of the nail. One characteristic, commonly recognized as existing in all french manicures or pedicures is the creation of a uniform boundary which visually distinguishes the tip and base portions of the nail. This visual boundary is important in recognizing or identifying the french manicure or pedicure style and is further characterized by having a substantially curvilinear configuration. Further, the curved visual boundary extends along and substantially corresponds to the natural transverse curvature or contour of the nail.

Other styles of cosmetic nail treatment are generally similar but clearly distinguishable from the french manicure. Such similar styles include an "American" style comprising a white or off-white tip and the application of one of a variety of different color nail polishes to the base of the nail. The distinguishing features between the french manicure and the American manicure are known to professional personnel as well as the large number of women who take great pride in properly caring for their fingernails and who prefer the french manicure or American manicure style. A characteristic common to both the french manicure and the American manicure, as well as other similar styles of cosmetic nail treatment, is the precise definition of the aforementioned visual boundary or demarcation, which exists between the tip of the nail and the base of the nail. The creation of this distinguishing characteristic, while a necessary visual component of the preferred french manicure style, is recognized as being somewhat difficult to create, even by practiced professionals specializing in cosmetic nail treatment.

The popularity of the french manicure or pedicure style has led to a number of prior art attempts to develop a technique and/or instrumentation which allows both cosmetic nail professionals as well as the average person, to quickly and easily perform a french manicure treatment. Specifically including the precise forming of the identifying and characteristic demarcation or boundary between the tip and base portions of the nail. By way of example, such known or prior attempts include the use of one or more shield structures dimensioned and configured to fit over a women's finger nails in a manner which allows the exposure of a tip of the nail and supposedly facilitates the formation of the demarcation boundary between the tip and base portions. Fingernail or toenail shields of this type exist in a variety of different structures, shapes, forms, etc. Regardless of their individual structures, all are primarily designed to segregate the outermost tip portion of the nail in a manner which initially creates a false demarcation line about which a white or off-white polish can be applied. The intended purpose of such structures is to precisely form the intended curved boundary between the tip and base portion of the nail.

Other attempts to perform a french manicure style nail treatment include the application of a tape or like adhesive backed, flexible material to the nail in a manner which also exposes the tip of the nail and attempts to shield the base portion from the application of the white or off-white polish. The tape or like material is intended to be applied in a manner which at least partially defines the intended curved configuration of the demarcation line. Other examples of known attempts to facilitate the performance of a french style manicure or pedicure include the mounting or attachment of decals in the form of false nail tips. Typically, such structures have been pre-colored in the appropriate shade to present the appearance of a french manicure type of cosmetic treatment.

While the above described attempts to facilitate the performance of preferred cosmetic treatments to the nail may, at least to some extent, enhance the ability of the average person to treat their own nails, it is generally accepted that such known techniques suffer from a plurality of problems or disadvantages. In addition, they do not effectively provide a method which assures the quick and easy performance of all aspects of an intended cosmetic treatment such as, but not limited to, the french manicure style. Such disadvantages include difficulty in fitting or applying the various shield structures to nails of various sizes and configurations. Also attachment of such structures has been found to be difficult and imprecise resulting in an unacceptable appearance of the visual demarcation boundary which, as set forth above, characterizes a french manicure style of cosmetic treatment. Also known techniques and implements of the type described above are time consuming based, at least in part, on required delays needed to allow certain painted or polished portions of the fingernail or toenail to dry before the shield type implements, tapes, decals, etc. can be removed and other portions of the nail can be treated.

Therefore, it is recognized that there is a significant and long existing need for a product and an attendant technique or method which facilitates the cosmetic treatment of person's nails, particularly when it is desired to perform a french style manicure or pedicure. Further, such an improved product, in at least one embodiment be made available as a kit assembly to better facilitate performance of the attendant method. Also, the method of the present invention should provide for the accurate but simple and quick formation of the required demarcation segment or curved line which serves to visually segregate the tip and base portions of the nail and which, at least to some extent, identify the french manicure style of cosmetic treatment. Further, such an improved kit assembly and method should be capable of being quickly and easily utilized by professionals and non-professionals alike, thereby allowing the average person to perform a french manicure style of cosmetic treatment on ones own nail.

SUMMARY OF THE INVENTION

The present invention is directed towards a kit assembly and a method or technique for performing a cosmetic treatment on either the fingernails or toenails of a person. More specifically, kit assembly and attendant method of the present invention is intended to facilitate the performance of a french style manicure or pedicure but, as will described in greater detailed hereinafter, is also capable of performing cosmetic nail treatments representative of a number of different styles in addition to the french manicure style. The kit assembly of the present invention comprises a plurality of different compositions, preferably supplied in solution form. Each of the solutions are provided in separate containers and, dependent upon their intended purpose, the containers for each of the plurality of solutions may also include an individual applicator. The individual applicators may be in the form of a brush or like implement of the type generally known in the art and commonly used to apply polish to fingernails or toenails.

The present invention also contemplates a number of different kit assemblies which may differ from one another by providing one or more polishes of different colors. For example, in that each of the various kit assemblies of the present invention are generally intended to provide a french manicure style of cosmetic treatment, the plurality of different solutions include at least a white or substantially off-white first color polish. Each of the plurality of kit assemblies contemplated in the present invention should also include at least a second color polish, differing from the white or off-white first color polish but being complementary thereto so as to accomplish the aforementioned french style manicure or pedicure. The second color polish may or may not be translucent and, by way of example only, may include a variety of different colors such as sheer pink, sheer beige, twilight white, twilight gold, twilight silver, etc. Each of these colors may be primarily designed for, but are not limited to use during specific events or times. For example, the pink and beige colors may be more applicable for every day use. The twilight white may be most appropriate for use during the twilight or evening hours or for special occasions such as weddings, graduations, baptisms, etc. The gold and/or silver colors may be the most decorative colors and accordingly would perhaps be more appropriate for wear during holidays such as Christmas, New years, birthdays, etc. Naturally, the second color polish, being clearly distinguishable from the white or off-white first color polish, could vary greatly in that a variety of different colors could be supplied. Also it is emphasized that the kit assembly of the present invention is not intended to be limited to the inclusion of a white or off-white first color polish in combination with only one of a plurality of second color polishes of the type set forth above. To the contrary additional versatility may be incorporated in anyone of the kit assemblies by including numerous variations of the white or off-white first color polish with a plurality of other color polishes, rather than just one.

Another feature of the kit assembly of the present invention, as well as the method and technique of performing a preferred cosmetic nail treatment, is the inclusion of a shaping solution and a shaping implement. As set forth above, an important and readily identifiable characteristic of a french style manicure or pedicure is the formation of a demarcation segment on the nail being treated. The demarcation segment is disposed and configured to visually distinguish different portions of the nail being treated. More specifically, and as set forth above, the french style manicure or pedicure is characterized by tip of the nail being painted or polished with the aforementioned white or off-white color or an acceptable variation thereof. The base of the nail should therefore be clearly segregated from the tip along a visually distinguishable boundary defined by the aforementioned demarcation segment. In addition this demarcation segment should most preferably be in the form of a "perfect curve" more realistically defined by the demarcation segment having a curvilinear configuration which substantially corresponds to at least a portion of the natural, transverse curve or contour of the nail. As such, the curvilinear line defining the demarcation segment is disposed in contiguous relation with both the tip and the base portion of the nail and thereby serves as the aforementioned visual boundary between these two intentionally distinguishable portions of the nail.

In order to facilitate the rapid, efficient and accurate forming of the demarcation segment, a shaping solution is applied to the base portion of the nail subsequent to the painting or polishing of the tip portion thereof. The tip portion has the white or off-white first color polish applied in a somewhat conventional fashion using an applicator brush typically included with the container in which the first color polish is supplied. Subsequently, a specifically structured shaping implement is utilized to apply the shaping solution. The shaping implement preferably comprises a somewhat elongated brush having a distal end in the form of a brush head. The brush head comprises a plurality of bristles which are at least partially submerged or placed in contact with the shaping solution. The shaping solution is then applied to the base portion of the nail in a manner such that only the outermost extremity of the collective array of bristles defines or forms the curvilinear demarcation segment. More specifically, the demarcation segment is formed by operatively moving or positioning the brush head through a "wiping action" which may be generally described as a reciprocal, side to side movement somewhat similar to the wiping action provided by a wind shield wiper on a conventional motor vehicle. In performing the side to side movement of the wiping action, the outermost extremities of the collective array of bristles passes along and thereby define the curvilinear demarcation segment. The shaping solution is formulated to remove any excess first color polish (white, off-white or preferred variation thereof) existing beyond the curvilinear demarcation segment on the base portion of the nail. Selective positioning and precise configuring of the preferred demarcation segment is thereby quickly, efficiently and accurately established. The shaping solution may be formulated as a solvent or more specifically an air drying solvent such that once applied in the manner set forth above, it quickly dries on the nail thereby allowing the remainder of the cosmetic treatment to proceed rapidly.

Additional steps in the preferred method of forming the french style manicure or pedicure include the subsequent polishing of the entire nail with the at least one second color polish. The preferred method of the present invention may also include the application of a protective top coat to the entire nail. The protective top coat is included as one of the aforementioned compositions provided in at least one of the preferred embodiments of the present invention. The top coat is formulated to physically protect and resist damage to the first and second color polishes and may also facilitate drying or setting of the polished nail surface. Further, the top coat may be clear, colorless and is specifically structured to provide a lustrous sheen to the nail surface.

Accordingly, it should be readily apparent that the kit assembly and the attendant method for applying the various compositions or solutions to the nail being treated, overcome many if not all of the problems and disadvantages existing with known or prior art products or techniques. Importantly, the kit assembly and method of the present invention allows for the average person, having no previous experience to quickly, easily and accurately perform a cosmetic treatment preferably, but not necessarily, in the french style without requiring the services of a professional manicurist.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As shown in the accompanying Figures, the present invention is directed towards a kit assembly generally indicated as 10 and an attendant method of performing a cosmetic treatment on either the fingernails or toenails of a person. In particular, the kit assembly and method of the present invention are specifically, but not exclusively, intended to facilitate the performance of a french style manicure or pedicure as generally disclosed in the descriptive representations of the fingernail shown in FIGS. 3 through 7.

Figure 1:
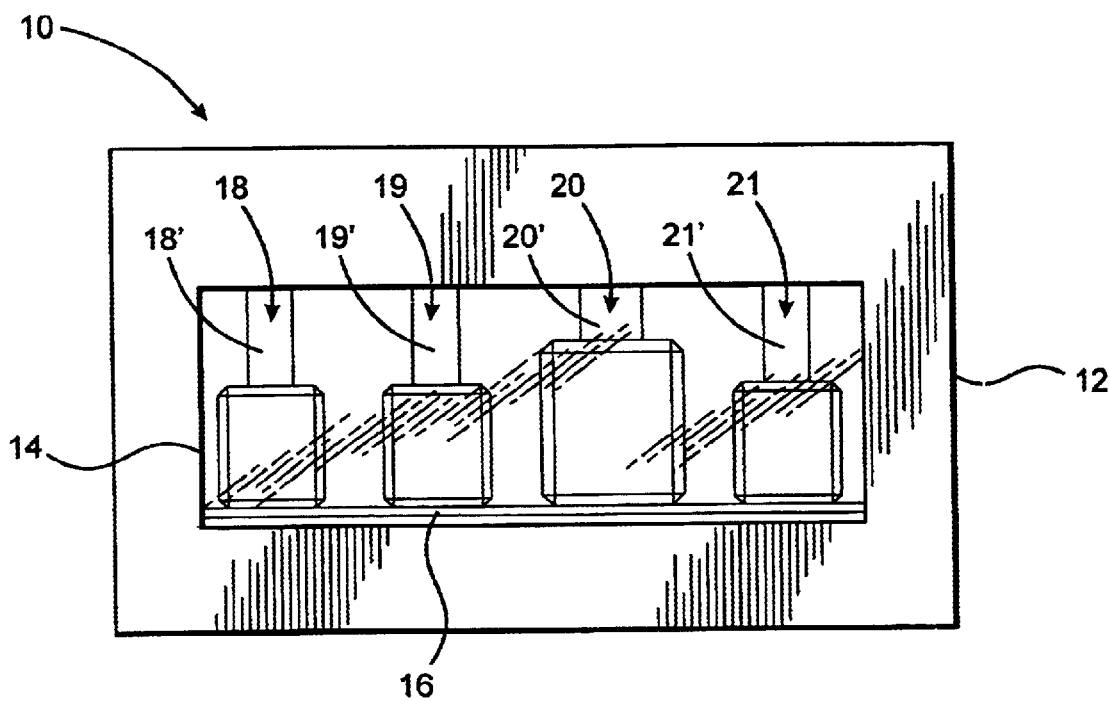
FIG. 1 is a front plan view of a kit assembly of the present invention.

With reference to FIG. 1, the kit assembly of the present invention is collectively contained within appropriate packaging or container 12, which may include a display window or the like 14 formed therein. A mounting or support structure 16 is disposed on the interior of the packaging 12 or made a part of the blank which forms the packaging 12.

In either embodiment, the structure 16, as well as other support or connecting members within the packaging 12 is disposed and configured to removably support a plurality of containers 18, 19, 20, and 21, which may vary in number, configuration, dimension and capacity. Each of the containers 18 through 21 are structured to retain one of a plurality of compositions, preferably in solution form, to be applied to the nail, generally indicated as 25, being treated. Each of the containers 18–21 include a closure or cap 18', 19', 20', 21', at least some of which are secured to an applicator device, preferably in the form of a brush as clearly indicated in FIGS. 4 through 7. Each of the applicator brushes are indicated by a common reference numeral 24.

In a preferred embodiment, as disclosed in FIG. 1, the kit assembly 10 comprises the plurality of compositions, each provided within the respective containers 18–21, including at least a first color polish, such as within container 18 and at least a second color polish, such as within container 19. The first color polish preferably comprises a white or off-white color, or a preferred variation thereof, especially when the cosmetic treatment to be applied to the nails 25 is intended to be in the french manicure style. The second color polish maintained within the container 19 may be any one of a variety of different colors which compliment the white or off-white first color polish but which are visually distinguishable therefrom. The colors represented in the at least one second color polish may also be those colors traditionally accepted as being applied to the nail during a french manicure. However, the color of the at least one second color polish may vary greatly and may be any one of a large number of different colors, complimentary to the white or off-white first color polish and may be specifically designed for every day or special event usage.

A preferred embodiment of the kit assembly 10 also includes a shaping solution supplied within the container 20 and formulated to comprise a solvent and/or more particularly an air drying solvent. As such, the shaping solution dries rapidly subsequent to being applied to the nail in the manner described hereinafter, specifically with reference to FIGS. 3 through 7. In addition, the kit assembly 10 of the present invention may also include a protective solution, supplied within the container 21, which is formulated to overlie, protect and provide a lustrous finishing sheen to the nail 25, once the first color polish and second color polish have been applied to the nail 25 in the intended manner.

Figure 2:
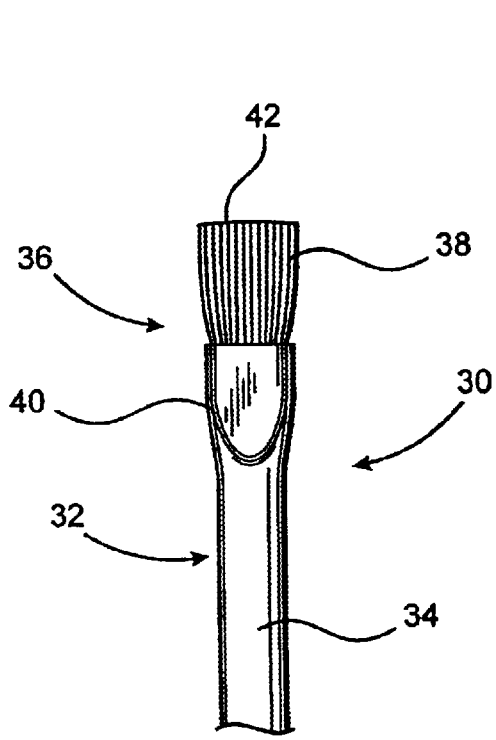
FIG. 2 is a front view in partial cutaway of a shaping implement included in the kit assembly of the embodiment of FIG. 1.
Figure 3:
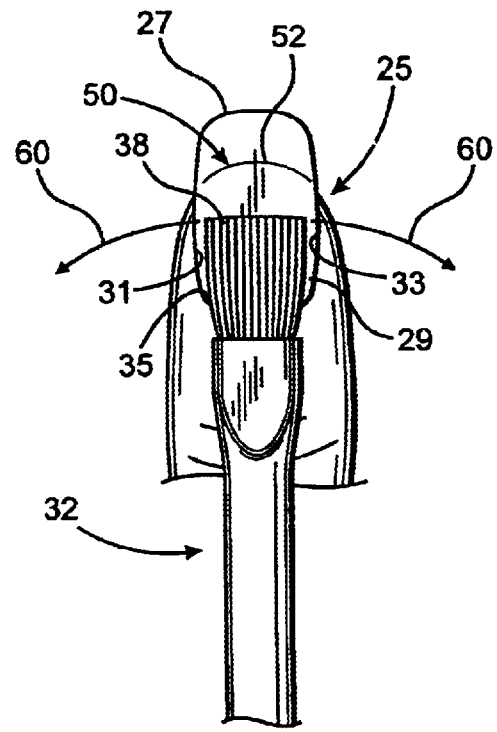
FIG. 3 is a top view in partial cutaway indicating the operative positioning and movement of the shaping implement relative to a nail being treated utilizing the kit assembly of the present invention.

Another feature of the kit assembly 10 of the present invention is the inclusion of a shaping implement generally indicated as 30. The shaping implement 30 is preferably, but not necessarily, defined by a brush 32 having a handle 34 with a configuration which is sufficiently elongated and/or otherwise dimensioned and configured to be easily gripped by the hand of a user. The shaping implement 30, in the form of the brush 32, also includes a brush head generally indicated as 36. The brush head 36 includes a plurality of bristles 38 secured by a gripping portion 40, which may crimped or otherwise structured to secure the plurality of bristles 38 in a grouped array. As shown in FIGS. 2 and 3, the plurality of bristles 38 at least partially define the distal end of the shaping implement 30 and include a distal extremity 42 generally defined by the outer most ends of the collected array of bristles 38. Further, in at least one embodiment the bristles 38 are sufficiently dimensioned and configured to overlie a predetermined portion of the nail 25 and/or base 29 thereof, such as at least a majority thereof. However, it is emphasized that the size and shape of the brush head 36 and/or the bristles 38 may vary and be such so as not to cover or overlie a majority of the nail 25 or base 29. Also, the bristles 38 are preferably formed of a material having a predetermined texture which is sufficient to facilitate the even application or "spreading" of the shaping solution on a predetermined portion of the nail 25. With primary reference to FIGS. 2 and 3, the nail 25 will be described as including a tip portion 27 and a base portion 29. The base portion 29 extends between and is substantially surrounded by the cuticle line, including opposite sides 31 and 33 and bottom 35.

While it is emphasized that a preferred embodiment of the shaping implement 30 is in the form of the previously described brush. It is recognized that other shaping implements or devices can be utilized to facilitate the formation of the demarcation segment. More specifically, another embodiment intended to be included as a possible shaping implement within the spirit and scope of the present invention comprises utilization of an elongated flexible material string, ribbon or like structure. In use, the string or ribbon is exposed to the shaping solution in a manner which will facilitate transfer of the shaping solution from the string or ribbon onto the base portion of the nail, as described. Further, application of the shaping solution to the nail also involves a reciprocal "back end forth" wiping action, wherein the string or ribbon is applied in a manner which serves to configure the demarcation segment in the recognized manner, as described above, of the french manicure style.

In addition, the shaping implement may assume a variety of other structural configurations and be formed, at least in part, from a variety of different materials. The primary functional and structural criteria for the shaping implement is of course the application of the shaping solution to a base portion of the nail in a manner which facilitates or defines the formation and predetermined configuring of the aforementioned demarcation segment. Therefore, in addition to the embodiments set forth above, the shaping implement may be hand held and may have an applicator portion which itself has an appropriate configuration, such as a curved shape which is also adequately dimensioned, to facilitate the formation of the preferably curvilinear configuration of the demarcation segment. The materials from which a modified shaping implement may be at least partially formed include a variety of natural or man made cloth materials including cotton, nylon, etc.; as well as other types of materials including sponge, cork, paper, fiberglass, and even a variety of wood, plastic, or metallic material compositions. Also a modified structural implement having an end portion covered with an applicable material of the type set forth above and generally of similar or equivalent structure as a "Q-tip" device or other small, elongated shaft having a material covered end, may also be utilized. Regardless of the specific structure, dimension, configuration or material of the structurally modified shaping implement utilized, the positioning of the implement, once exposed to the shaping solution, may generally be described as a side-to-side, normally reciprocal wiping action resembling a "windshield wiping" action, as further set forth herein.

As set forth above, the french manicure style of cosmetic treatment is identified and/or characterized by the provision of a demarcation segment, generally indicated as 50. The demarcation segment 50 is more specifically defined by a line formed on the outer surface of the nail 25 which serves as a visual boundary and which visually segregates distinguishable portions of the nail 25, specifically including the tip portion 27 and the base portion 29. As such, the visually observable features which characterize the presence of a french manicure style cosmetic treatment include the tip 27 having the first color polish, being white or off-white, applied thereto. In addition, the base 29 of the nail has a complimentary but clearly different second color polish applied thereto. In typical fashion, the second color polish is preferably applied over the entire nail subsequent to the application of the white or off-white first color polish to the tip 27 and after the first color polish has adequately dried or set on the tip 27.

Further with regard to the demarcation segment 50, it is preferably defined by a line 52 having a curvilinear configuration which corresponds to the natural transverse curvature or contour of the nail. Therefore the demarcation line 52 is more accurately defined by the boundary between the first color polish applied to the tip 27 and the visually distinguishable, contiguously disposed base 29 of the nail 25. The demarcation segment 50 and more specifically the curved line 52 can thereby be described as being disposed in contiguous relation to both the tip 27 and the base 29 in that it forms a visually segregating boundary there between.

Figure 4:
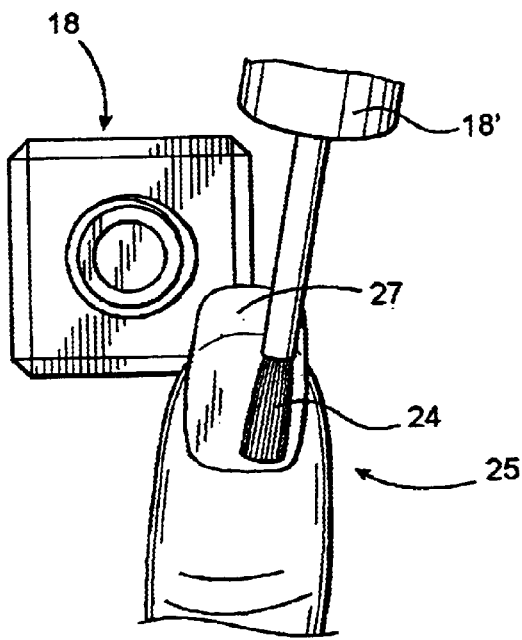
FIG. 4 is a top view demonstrating one step of a method of providing a preferred cosmetic nail treatment in accordance with the present invention.
Figure 5:
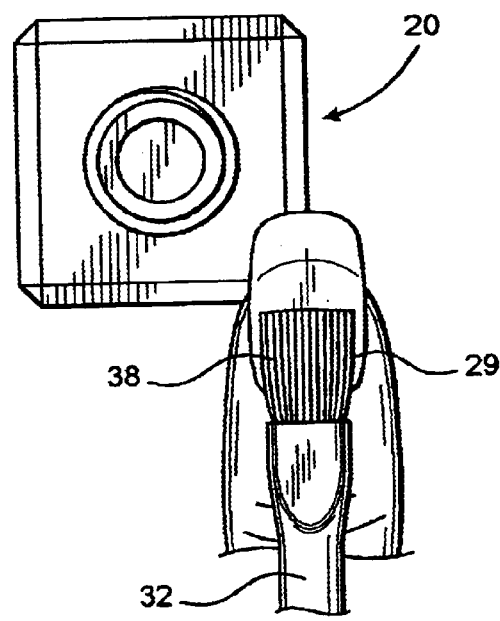
FIG. 5 is a top view demonstrating another step in the method of applying a preferred cosmetic treatment to a nail.

Accordingly, the attendant method of the present invention includes a first color polish as supplied within the container 18 being first applied to the tip 27 of the nail 25 as shown in FIG. 4. An applicator brush or like implement 24 accompanying the container 18 may be used to apply the first color, white or off-white polish. In doing so the inadvertent spreading of the first color polish onto at least an adjacent portion of the base 29 may be inevitable. Therefore, as shown in FIG. 5, the formation of the demarcation segment 50, more specifically defined by a curved demarcation line 52, is shaped into an intended "perfect curve". The resulting curvilinear configuration of the demarcation line 52 may of course not be geometrically "perfect", but preferably conforms to the natural transverse curvature or contour of the nail 25 being treated. As shown, the demarcation line 52 is formed by coating or otherwise applying the shaping solution to the plurality of bristles 38 of the shaping implement 30 or brush 36. The shaping solution, is provided in the kit assembly 10, as in container 20 and is preferably formulated as a solvent. The shaping solution is then applied to the base 29 of the fingernail 25 in a manner which accurately removes all of the excess first color polish from any portion of the base 29 existing beyond the demarcation line 52. As such, the head 36 of the brush 32 is operatively oriented in the manner shown in FIG. 3, wherein the head 36 extends towards the tip 27 of the nail 25. Once this operative orientation is accomplished and the plurality of bristles 38 are in direct confronting engagement with the surface of the base 29, the user movably positions the bristles 38 through a "windshield wiping" action which may be a somewhat side-to-side, reciprocal movement as indicated by directional arrows 60. This wiping action occurs concurrently to the distal extremities or collective distal ends of the bristles 38 being in aligned relation to the intended position of the curved demarcation line 52. As such, all excess first color polish will be removed from the base 29 and the curved demarcation line 52 will be accurately and easily formed by operatively orienting or moving the brush head 36, including the bristles 38, through the aforementioned "windshield wiping" action as indicated by directional arrow 60. Once this has been accomplished the nail drys almost instantly or is then allowed to quickly dry in very a short amount of time due to the air drying capabilities of the solvent from which the shaping solution is formulated.

Figure 6:
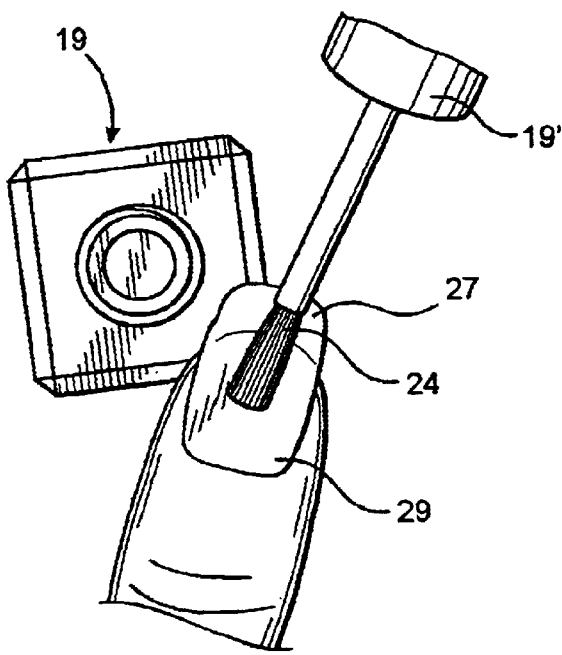
FIG. 6 is a top view demonstrating yet another step of the method of cosmetic nail treatment.
Figure 7:
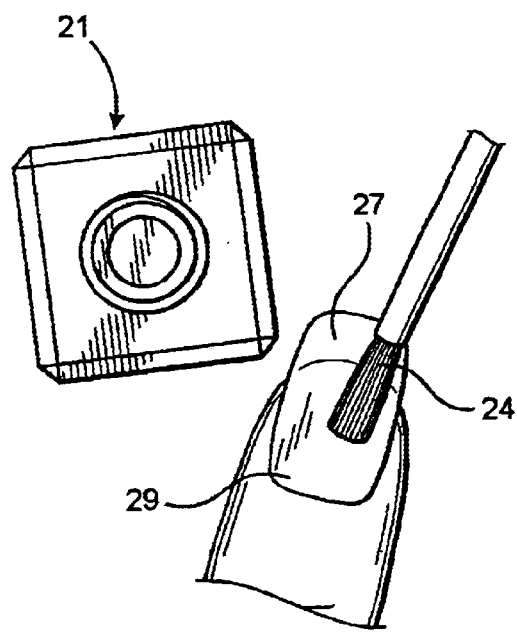
FIG. 7 is a top view demonstrating yet another step in the method of cosmetic nail treatment.

As shown in FIG. 6, a selected at least one second color polish, of the type initially supplied in the container 19, is then applied, using the conventional applicator brush 24, to the entire nail and in overlying relation to both the base 29 and tip 27. The complimentary coloring between the first and second color polishes will further enhance the aesthetic appearance of the nail 25 upon completion of the polishing step represented in FIG. 6. It is also noted that at least the second color polish is preferably formulated to be sheer and therefore can be applied to both the tip 27 and the base 29 in the manner described.

In addition, at least one embodiment of the method of the present invention may also include the application of a protective solution to the entire nail, including the base 29 and the tip 27 wherein the protective solution, originally supplied within the container 21, may be clear in color and further formulated to offer the aforementioned protective features, as well as provide a lustrous finishing sheen to the nail.

It is again emphasize that the kit assembly 10 as well as the method associated therewith may be applied in the same fashion to both fingernails and toenails in order to create a french style manicure or pedicure.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,
What is claimed is:

1. A method of performing a cosmetic treatment on a person's nail, said method comprising;
   a) applying a first color polish to a tip of the nail,
   b) applying a shaping solution to a base of the nail, and
   c) manipulating the shaping solution on the base of the nail to remove at least some of said first nail polish from said tip of the nail and thereby define a demarcation segment substantially between visually distinguishable portions of the nail.

2. A method as recited in claim 1 comprising forming the demarcation segment in segregating relation to the tip of the nail and the base of the nail.

3. A method as recited in claim 2 comprising operatively positioning a shaping implement on the base to configure the demarcation segment.

4. A method as recited in claim 3 comprising shaping the demarcation segment to substantially correspond to the natural transverse contour of the nail.

5. A method as recited in claim 4 comprising movably orienting the shaping implement in confronting relation to the base of the nail so as to shape the demarcation segment into a curvilinear configuration.

6. A method as recited in claim 3 comprising movably orienting the shaping implement in confronting relation to the base of the nail so as to form the demarcation segment into a curvilinear configuration.

7. A method as recited in claim 6 comprising orienting a distal end of the shaping implement in a direction substantially towards the tip of the nail when the shaping implement is in the operative orientation.

8. A method as recited in claim 7 comprising moving the distal end of the shaping implement between opposite sides of the base of the nail in a substantially wiping action so as to facilitate the forming of the demarcation segment in a curvilinear configuration substantially corresponding to the natural transverse contour of the nail.

9. A method as recited in claim 8 comprising defining the shaping implement as a brush and the distal end thereof as a brush head including a plurality of bristles.

10. A method as recited in claim 9 comprising defining the shaping solution as a solvent.

11. A method as recited in claim 10 comprising applying a second color polish to at least the base of the nail subsequent to the application of the shaping solution.

12. A method as recited in claim 11 comprising applying the second color polish concurrently to both the tip and the base of the nail.

13. A method as recited in claim 11 further comprising applying a protective coating in overlying relation to both the first color polish and the second color polish.

14. A method as recited in claim 7 comprising reciprocally moving the distal end of the shaping implement between opposite sides of the base of the nail in a substantially windshield wiping action so as to facilitate formation of the demarcation segment into a substantially curvilinear configuration corresponding to the natural transverse contour of the nail.

15. A method as recited in claim 3 comprising defining the shaping implement as a brush and the distal end thereof as a brush head including a plurality of bristles.

16. A method as recited in claim 15 comprising defining the shaping solution as a solvent.

* * * * *